United States Patent [19]

Whitehead et al.

[11] Patent Number: 5,065,758

[45] Date of Patent: Nov. 19, 1991

[54] COLD PACK FOR TREATMENT OF INJURIES

[76] Inventors: James L. Whitehead, 930 S. Davis, McMinnville, Oreg. 97128; Leland D. Chapman, 65579 E. Alpine Way, Rhododendron, Oreg. 97049

[21] Appl. No.: 507,300

[22] Filed: Apr. 10, 1990

[51] Int. Cl.$^5$ .............................................. A61F 7/00
[52] U.S. Cl. ................................... 128/402; 128/399; 128/381
[58] Field of Search ............................... 128/379–382, 128/399–403, 82.1

[56] References Cited

U.S. PATENT DOCUMENTS

| 4,114,620 | 9/1978 | Moore et al. | 128/400 |
| 4,592,358 | 6/1986 | Westplate | 128/402 |
| 4,676,247 | 6/1987 | Van Cleve | 128/403 |
| 4,805,619 | 2/1989 | Swearingen | 128/380 |
| 4,846,176 | 7/1989 | Golden | 128/379 |
| 4,886,063 | 12/1989 | Crews | 128/403 |

FOREIGN PATENT DOCUMENTS 0036910 10/1981 Australia ............................ 128/82.1

Primary Examiner—Robert A. Hafer
Assistant Examiner—Kerry Owens
Attorney, Agent, or Firm—Robert L. Harrington

[57] ABSTRACT

A cold pack for treating an injury of a subject person. A cooling media, e.g. of BLUE ICE is encased in elongate plastic closed end cylinders. The cylinders are inserted in parallel pockets formed in a wrapper, e.g. made of cloth with the interconnecting cloth material forming flexible hinges between the cylinders. Straps provided on the wrap enable the application of the pre-chilled cold pack to be applied to the injured area of the subject person. The container and plastic partially insulate the cooling media which has the doubly beneficial effect of reducing the cooling effect and extending the life of the cold pack.

7 Claims, 2 Drawing Sheets

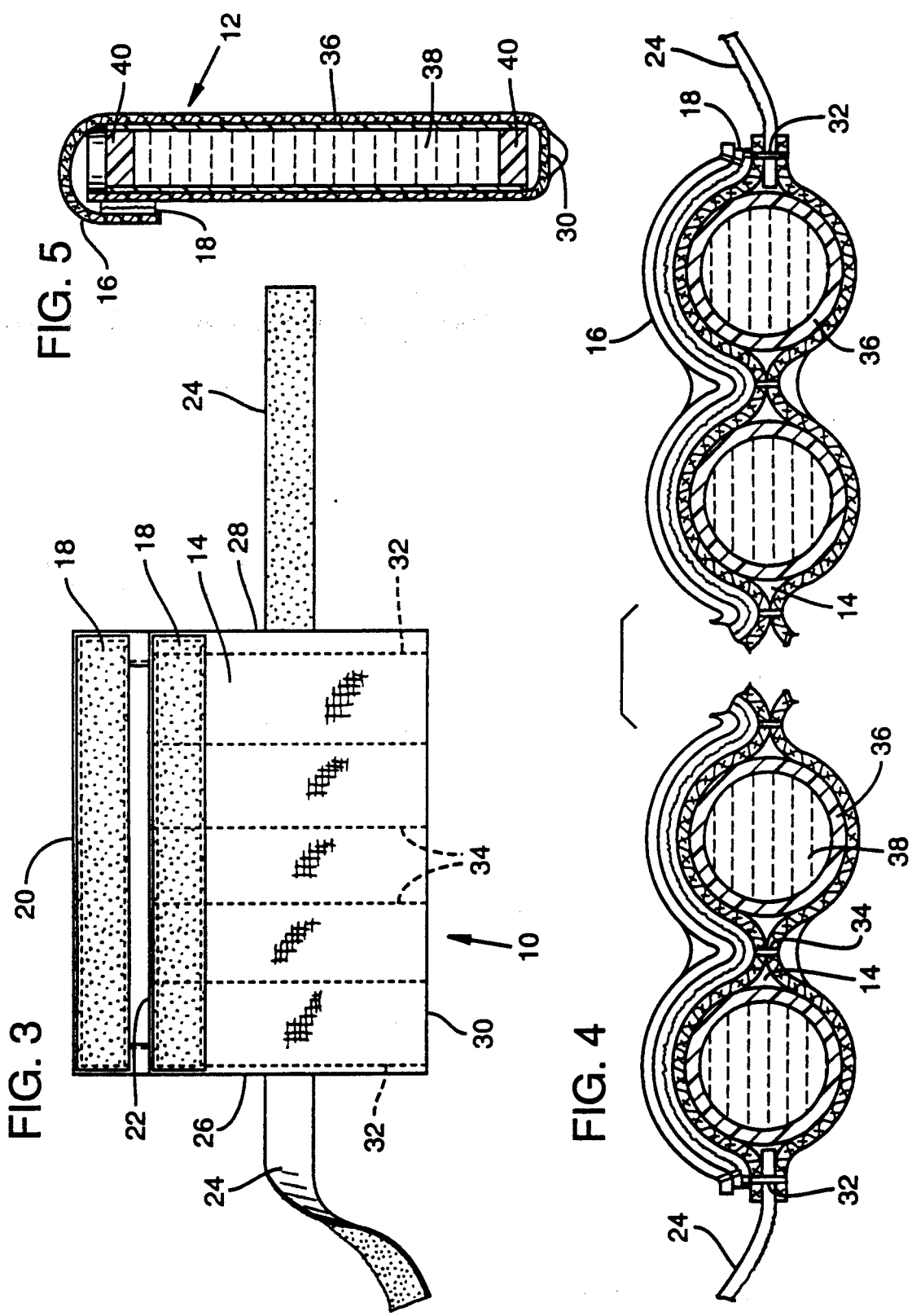

COLD PACK FOR TREATMENT OF INJURIES

BACKGROUND INFORMATION

1. Field of the Invention

This invention relates to a treatment of muscular injuries such as sprains or strains and in particular it relates to a cold pack to be applied to an area of the injury.

2. Background of the Invention

It is known that it is beneficial to treat injuries to the muscles such as strains or sprains by the immediate application of a cooling device to the injured area. Immediate cooling of the injured area provides many physiological benefits such as limiting the amount of swelling etc., and aids in reducing the discomfort to the individual.

Individuals involved in competitive sports are most likely to suffer an injury of this type, particularly those involved in a contact sport such as football. Since sprains and strains are a possibility in any football game, the coaches and trainers are prepared to treat these injuries. Typically, when an injury occurs, ice is utilized to provide the means to cool the area. In most cases, the ice is on site, either in bulk in a cooler or packed in individual bags. When an injury occurs, a bag of ice is applied to the injured area.

Although ice provides the desired cooling effect, its use has several disadvantages.

Ice, whether it is stored in bulk or in individual bags, tends to solidify into a solid mass. This means that it ha to be broken into smaller usable pieces. If it is in a bag, it is difficult to break up the ice without causing damage to the bag creating the problem of leakage as the ice melts. If the ice is not broken into small enough pieces, the bag will not conform to the area of the injury, and the desired cooling effect to the whole injured area does not occur. Ice is too cold, that is, its heat absorption rate is too high and causes too much discomfort to be applied to an injury on a continuous basis. Therefore, the ice bag is commonly applied intermittently.

There is not an effective and easy method of retaining the ice bag on the injured area, especially when the ice bag has to be applied for short periods of time. In addition, as the ice melts within the bag, the shape of the bag changes requiring repositioning of the bag on the injury. Furthermore, the ice melts quickly and must be replenished over the course of a couple of hours, a common time lag between injury and treatment at a medical facility.

BRIEF SUMMARY OF THE INVENTION

The cold pack of the present invention is a self contained wrap. In the preferred form, the wrap includes a flexible or pliable fabric container that has individual parallel compartments or pockets that retain liquid filled elongate tubes. The wrap is normally chilled prior to use to freeze the liquid in the tubes. Preferably the liquid is a slow melting liquid such as that which is referred to as BLUE ICE. The tubes provide the secondary function of insulating the frozen liquid to facilitate slowing of the melting process.

The chilled wrap, referred to as a cold pack is applied to an injury such as a sprain by wrapping the cold pack around the injured area. Retaining straps are provided to secure the cold pack in position and to apply the cold pack in a compressive manner as required.

The resilient container of the cold pack will conform closely to the surface area of the injury. The cold pack in contact with the injured area provides a cooling effect to the injury. The heat absorption rate of the cold pack is relatively low. This permits the continuous application of the cold pack to the injury without the discomfort of extreme cold experienced with the typical bag of ice.

The basically parallel arrangement of the semi-rigid tubes in the container provides rigidity along one axis and makes the pack highly suitable for use as a cold splint.

Other objects and advantages will be apparent upon examination of the drawings and the detailed description.

BRIEF DESCRIPTION OF THE DRAWINGS

FIG. 3 is a frontal view of the container minus the liquid filled tube;

FIG. 4 is a sectional view taken along view lines 4—4 of FIG. 2; and

FIG. 5 is a sectional view taken along view lines 5—5 of FIG. 2.

DESCRIPTION OF THE PREFERRED EMBODIMENT

Figure 1:
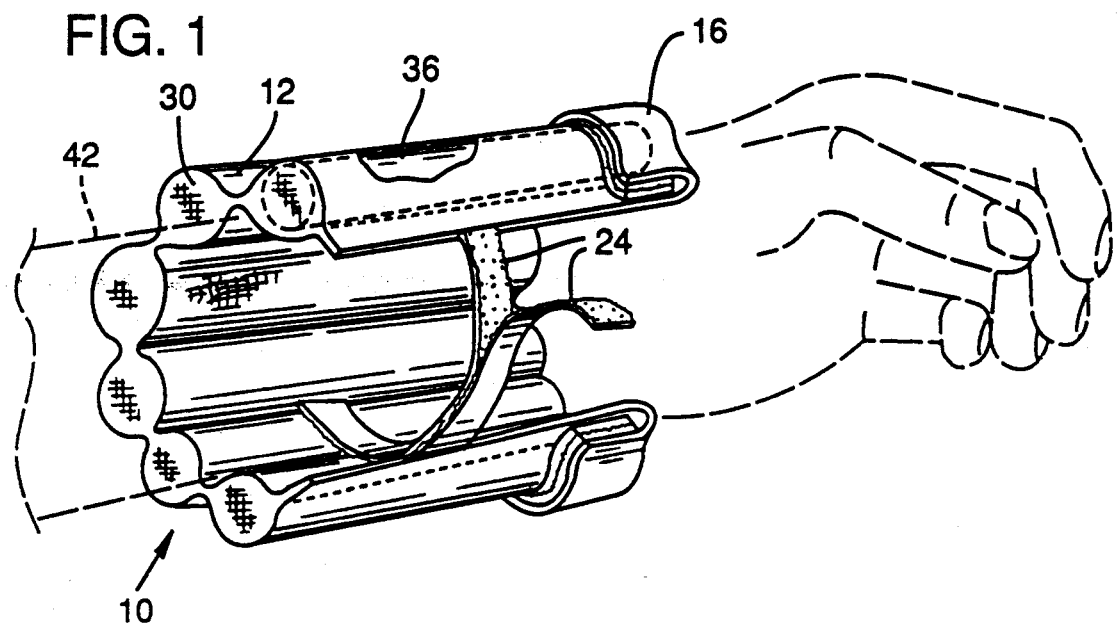
FIG. 1 is a view of a cold pack in accordance with the present invention.

Refer now to the drawings which illustrate one embodiment of the invention. FIG. 1 shows a cold pack or wrap having a container 12. The container 12 is subdivided into compartments or pockets 14 which house a plurality of tubes 36. A cover 16 that extends the width of the container 12 covers the open end of the compartments 14 to retain the tubes 36 in the compartments.

The construction of the container 12 will be described with reference to FIG. 3. The container 12 is preferably constructed of a washable pre-shrunk flexible fabric that is soft to the touch such as a brushed denim. The container 12 is constructed from a single piece of fabric as by sewing. The fabric is hemmed on all edges in a conventional manner. Self adhering strips 18, preferably of VELCRO, are attached at an upper edge 20 on one side of the fabric and at a lower edge 22 on the opposite side of the fabric. After the strips 18 are attached, the fabric (as shown in the figure) is folded partially onto itself (thus layered) with the lower edge 22 (as viewed in the figure) being below the upper edge 20. The fold of the fabric forms the bottom 30 of the container 12.

Elongated flat straps 24, incorporating a self adhering material, preferably of VELCRO, are positioned, one at side 26 and another at side 28 of the container 12, with an end of each strap inserted between the layers of the fabric. The straps are secured in position by seams 32 sewed near the edges of sides 26 and 28 in a conventional manner. Seams 32 extend from the bottom 30 of the container 12 to the edge 22.

The pockets of the container case are provided by multiple seams 34, parallel to each other and to seams 32. They are sewn at spaced intervals with each seam 34 extending from the bottom 30 to the edge 22. As shown in the FIG. 3, the distance between adjacent seams 34 and the distance between seam 34 and adjacent seam 32 is equal. The sewing of seams 32 and 34 binds the layered fabric together in a conventional manner and forms the tube receiving compartments 14 having an open end at edge 22.

The opposite end of the compartments are closed by bottom 30 which is the fabric folded onto itself. The distance between the seams determines the diametrical size of each compartment 14. The length of each compartment 14 is determined by the distance from the bottom 30 of the container 12 to the edge 22. The compartments 14 are sufficiently large so that the tubes 36 when inserted into the compartments will fit loosely which allows the tubes 36 to have limited lateral movement within the compartments 14.

Figure 2:
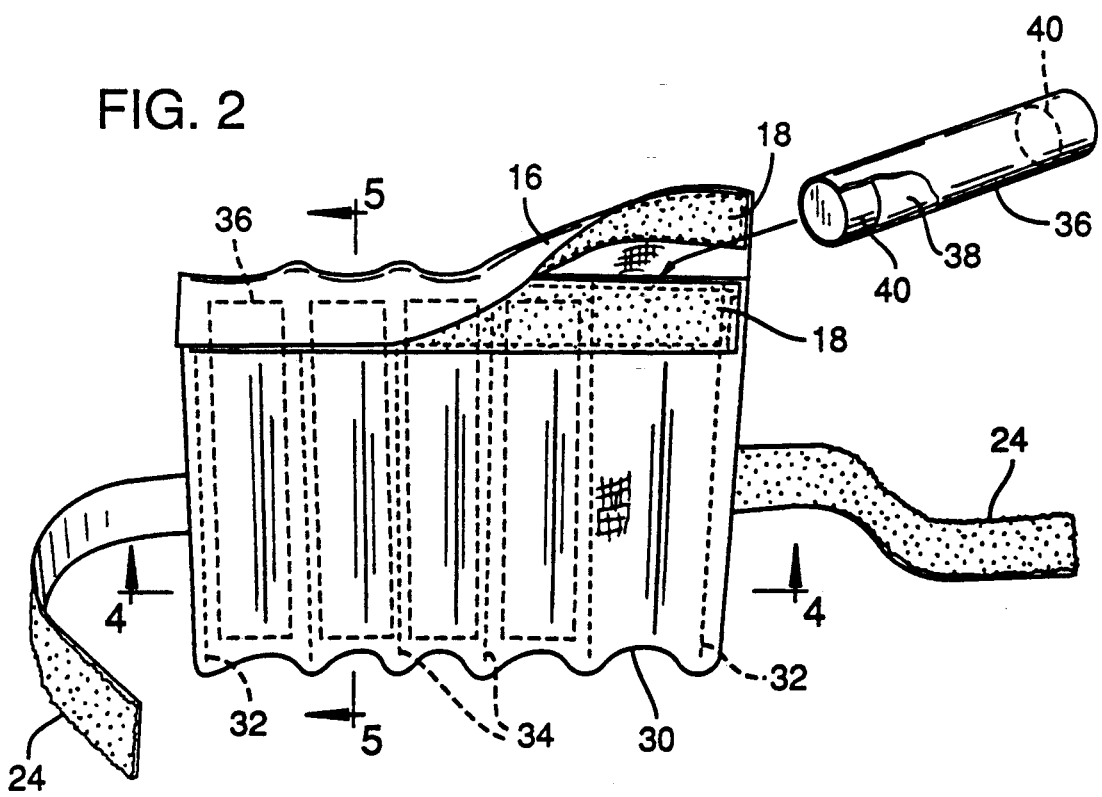
FIG. 2 is a frontal view of the cold pack of FIG. 1 showing the cover and the parallel arrangement of the compartments.

The cover 16 is provided to retain the tubes 36 in the compartments 14. The layer of fabric extending from the edge 20 to the edge 22 (as shown in FIG. 3) forms the cover 16. As shown in FIG. 2, the fabric is folded down to cover the tops (i.e the open ends) of the individual compartments 14.

While only one container 12 has been shown in the figures, it is obvious that it may have configurations other than the basic rectangular shape (i.e., triangular, circular etc.). The compartments 14 provided in the container 12 may vary in number and of course the compartments 14 may have different lengths to accommodate differing lengths of tubes 36. Multiple tubes 36 may also be inserted into each of the compartments 14 in an end to end relationship so that the pack 10 may have flexibility transverse to the seams 32 and 34 of the container 12. The containers 12 that accommodate the longer tubes 36 may be provided with additional straps 24 that would be placed strategically along the edges 26 and 28 of the container 12.

FIG. 2 illustrates the container 12 having tubes 36 inserted into the individual compartments 14. The tubes 36 are semi-rigid elongate hollow cylinders, preferably constructed of CPVC tubing, an acronym for chlorinated poly vinyl chloride, and is readily available in most hardware stores and home builder supply stores. The tubes are filled with a semi-liquid material 38, preferably BLUE ICE, available from the Gott Division, Rubbermaid, Inc. The ends of the tube 36 are sealed by plugs 40 inserted into the internal diameter of the tube 36 and secured as by gluing.

FIG. 5 shows a tube 36 inserted into a compartment 14 of the container 12. The cover 16 is in the closed position and is secured by the self adhering fasteners 18. The plugs 40 seal the ends of the tube 36 thus retaining the material 38 within the tube 36.

One method for filling the tubes 36 with material 38 and sealing the ends of the tubes with the plugs 40 is as follows. A temporary end cap (not shown) is placed on one end of a long length of tubing, e.g. several times as long as the tube 36. The tubing is filled with the material 38 and the tubing is placed in a cooling device, such as a freezer, with the length of the tubing oriented vertically with the open end of the tubing at the top. After the tubing filled with the material 38 has been sufficiently cooled, preferably to a temperature in the range of 0 to 5 degrees fahrenheit, the tubing is removed from the freezer, the temporary end cap is removed and the tubing is cut into the desired lengths of tubes 36 that will fit into the compartments 14 of the container 12. The material 38 is pushed out of each tube 36 until a length equal to the combined length of two plugs 40 is exposed. The exposed length is severed from the material 38 and set aside. The material 38 is pushed back into the tube 36 until the material 38 is inset from each end of the tube 36 a distance equal to the length of the plug 40. Into each end of the tube 36, a plug 40 is inserted and secured as by gluing. The gluing of the plugs 40 into each end of the tube seals the ends of the tube against leakage of the material 38 out of the tube 36.

As shown in FIG. 1, the cold pack 10 is applied to an area of an injury, such as a forearm 42 of an individual by wrapping the cold pack around the forearm 42 and securing it in position by utilizing the straps 24. The flexibility of the container 12 coupled with the tubes 36 fitting loosely in the compartments 14 allows the cold pack 10 to closely conform to the surface area of the injury. As shown, the compartments 14 and the tubes 36 contained therein are basically parallel to the forearm 42. The degree to which the straps 24 are tightened controls the compressive force applied to the injury by the pack 10.

The heat absorption rate of the pack 10 is basically controlled by having the mass of material 38 contained in the tubes 36 isolated (i.e. insulated) from the injury by the insulating quality of the fabric of the compartments 14 surrounding the tubes 36 and the relatively slow heat absorption rate of the wall of the tube 36 itself. By controlling the manner in which the pack is applied (i.e., controlling the contact area), the rate of heat absorption from the injured area by the pack 10 may be further controlled.

The tubes 36 placed in the compartments 14 of the container 12 in a basic parallel arrangement provides a rigidity to the container along the longitudinal axis (i.e., the length) of the compartments 14. The rigidity provided by the tubes 36 in the compartments 14 makes the cold pack suitable for use as a cold splint for bone fractures, immobilizing a joint such as a knee or elbow and other applications where rigidity is required.

Variations and modifications will be apparent to those skilled in the art. The scope of the invention is therefore not to be limited to the drawings and the preferred embodiments as detailed, but is to be determined by the appended claims.

We claim:

1. A cold pack for treating an injured area of a subject person comprising;

a plurality of rigid closed end cylinders, flexible connecting means interconnecting the cylinders in parallel side-by-side relationship, a cooling media characterized by its cooling property when exposed to ambient temperature, said cooling media encased in said plurality of cylinders to thereby provide a wrap of rigid side-by-side cooling media encased cylinders separated by flexible hinges, said rigid cylinders of a designated size and said flexible connecting means providing hinge connections between said rigid cylinders to permit the cold pack to be formed into a curve for wrapping around the injured area of a subject person.

2. A cold pack as defined in claim 1 wherein flexible retaining straps are provided for removably attaching the cold pack to the subject person over the injured area.

3. A cold pack as defined in claim 2 wherein the flexible retaining straps are a soft cloth that is comfortable in feel when applied to the skin of the subject person.

4. A cold pack as defined in claim 3 wherein the walls of the cylinders are a plastic material that insulates in part the cooling media within the cylinders and thereby the cooling action of the cooling media that both decreases discomfort and increases the cooling life of the cold pack.

5. A cold pack as defined in claim 4 wherein the cooling media is permanently encased in the cylinders, a container of flexible material is provided with side-by-side pockets, and the cylinders are removably encased in the pockets of the container enabling individual preparation including cleaning of the cloth material and placement of the cylinders for freezing in a cooling chamber.

6. A cold pack as defined in claim 5 wherein the cylinders are semi-rigid plastic of chlorinated poly vinyl chloride.

7. A method of treating an injury of a subject person that comprises;
   enclosing a cooling media in elongate rigid cylinders, enclosing the cylinders in a container of flexible material having side-by-side pockets receiving the cylinders and having flexible hinges between the pockets, said cylinders of a designated size and said hinges compatible therewith to permit forming of the cold pack into a curve, chilling the cooling media within the cylinders to a temperature substantially below room temperature, and
   wrapping the container with interconnected cylinders of the chilled cooling media around the injured area of a subject person.

* * * * *